United States Patent [19]

Fahmy et al.

[11] 4,279,897

[45] Jul. 21, 1981

[54] (ALKOXYCARBONYL)(ALKYL-)AMINOSULFENYL DERIVATIVES OF PHOSPHORAMIDOTHIOATE ESTERS

[75] Inventors: Mohamed A. H. Fahmy; Tetsuo R. Fukuto, both of Riverside, Calif.

[73] Assignee: The Regents of the University of California, Los Angeles, Calif.

[21] Appl. No.: 18,415

[22] Filed: Mar. 7, 1979

[51] Int. Cl.$^3$ .......................... A01N 57/30; C07F 9/24
[52] U.S. Cl. ................................ 424/211; 260/938; 260/968
[58] Field of Search ...................... 260/938, 968, 944; 424/211

[56] References Cited

U.S. PATENT DOCUMENTS 4,081,536 3/1978 Nelson .......................... 260/938 X

OTHER PUBLICATIONS

Marino, "Topics in Sulfur Chemistry", vol. 1, Sulfur–Containing Cations, (1976), pp. 3, 4, 5, 14 & 15.

*Primary Examiner*—Anton H. Sutto
*Attorney, Agent, or Firm*—Herzig & Walsh, Inc.

[57] ABSTRACT

A novel class of chemical compounds useful as pesticides consists of O,S-dimethyl N-(N'-alkoxycarbonyl-N'-alkylaminosulfenyl)phosphoramidothioates. The preparation of these compounds and their formulation to control insects are exemplified.

19 Claims, No Drawings

(ALKOXYCARBONYL)(ALKYL)AMINOSULFENYL DERIVATIVES OF PHOSPHORAMIDOTHIOATE ESTERS

BACKGROUND OF THE INVENTION

This invention relates to the general field of pesticides, and is particularly concerned with the production of insecticides for the control of household insects and crop insects, particularly the latter.

It is known that derivatization of the nitrogen atom of carbamate esters by different functional groups such as acyl, as disclosed in Fraser, J., Clinck, G. C., and Ray, R. C., J. Sci. Food Agr. 16, 615, 1965, dialkoxyphosphinylthio, as disclosed in Fahmy, M. A. H., Fukuto, T. R., Myers, R. O., and March, R. B., J. Agric. Food Chem. 18, 793, 1970, alkyl- and arylsulfenyl, as disclosed in Black, A. L., Chiu, Y. C., Fahmy, M. A. H., and Fukuto, T. R., J. Agric. Food Chem. 21, 747, 1973, aryl and alkylcarbamylosulfenyl, as disclosed in Fahmy, M. A. H., Chiu, Y. C., and Fukuto, T. R., J. Agric. Food Chem. 22, 59, 1974, and Fahmy, M. A. H., Mallipudi, N. M., and Fukuto, T. R., J. Agric. Food Chem. 26, 550, 1978, generally results in compounds of high insecticidal activity but of lower mammalian toxicity.

Derivatization of methamidophos (O,S-dimethyl phosphoramidothioate), an organophosphorus compound of high toxicity to both insects and mammals, has been limited to acyl groups as disclosed in Magee, P. S., Res. Rev. 53, 3, 1974. The N-acetyl derivative of methamidophos (acephate) is a commercial product of high insecticidal activity and relatively low mammalian toxicity.

The object of the present invention is to provide a novel class of stable sulfenyl derivatives of phosphoramidothioate esters which are effective pesticides, and procedure for preparing same.

SUMMARY OF THE INVENTION

The novel pesticidal compounds of the invention are O,S-dimethyl N-(N'-alkoxycarbonyl-N'-alkylaminosulfenyl)phosphoramidothioates. The compounds are thus N-(alkoxycarbonyl)(alkyl)aminosulfenyl derivatives of methamidophos, and are prepared by reacting methamidophos with N-chlorosulfenyl aliphatic carbamates, in a suitable organic solvent and in the presence of a hydrogen chloride acceptor such as pyridine.

The resulting compounds of the invention are effective against certain pests and insects by contact and systemic action, particularly including crop insects, and have reduced mammalian toxicity, as compared to the parent insecticide, methamidophos. Thus, the invention compounds, while having high toxicity toward certain pests or insects, are relatively safe to mammals. Such compounds are stable and can be stored at ambient temperature over extended periods of time without significant reduction of insecticidal effectiveness.

DETAILED DESCRIPTION OF THE INVENTION AND PREFERRED EMBODIMENTS

The sulfenyl derivatives of phosphoramidothioate ester compounds of the invention have the formula noted below:

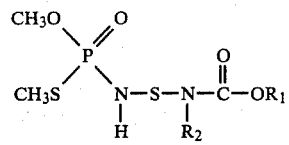

where $R_1$ and $R_2$ are alkyl groups. Thus, $R_1$ can be an alkyl group of from 1 to 12 carbon atoms, preferably 1 to 8 carbon atoms, free from nonaromatic unsaturation, e.g. from olefinic and acetylenic unsaturation, and can be straight or branched chain, including methyl, ethyl, propyl, isopropyl, butyl, isobutyl, tert.-butyl, pentyl, hexyl, isohexyl, heptyl, octyl, isooctyl, nonyl, isononyl, decyl, etc. $R_2$ can contain from 2 to 8 carbon atoms, preferably 2 to 4 carbon atoms, and can be straight chain or branched chain, preferably branched chain, as exemplified above, ranging from ethyl to octyl, preferably ethyl to butyl, and particularly isopropyl and tert.-butyl.

The carbamate ester compounds of the invention can be prepared by the following general reaction:

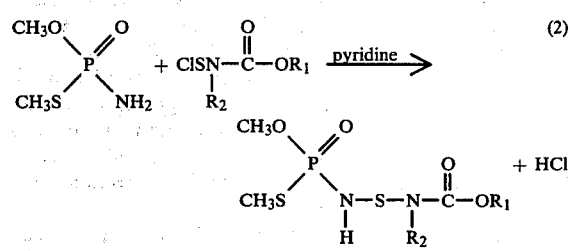

where $R_1$ and $R_2$ are as defined above.

The N-sulfenyl chlorides of alkyl alkylcarbamate intermediates in the above reaction can be prepared as described by Brown and Kohn in U.S. Pat. No. 3,843,689, by reaction between the aliphatic carbamate and sulfur dichloride in dichloromethane, using pyridine as acid acceptor.

Such N-chlorosulfenyl aliphatic carbamates are reacted with methamidophos according to the above reaction (2) in the presence of an equivalent amount or a small excess of a hydrogen chloride acceptor such as pyridine, in an organic solvent such as methylene chloride, chloroform or tetrahydrofuran, at temperature ranging from 0° C. to room temperature, about 20° C., preferably at reduced temperature, e.g. from 0° to 5° C.

The following are examples of preparation of the N-[(alkoxycarbonyl)(alkyl)aminosulfenyl]phosphoramidothioates of the invention.

EXAMPLE I

Synthesis of O,S-dimethyl N-(N'-propoxycarbonyl-N'-isopropylaminosulfenyl)phosphoramidothioate.

To a stirred mixture of 4.0 g (0.028 mol) O,S-dimethyl phosphoramidothioate, 2.2 g pyridine (0.028 mol) and 15 ml of anhydrous methylene chloride, chilled to 0°–5° C., was added dropwise 6.0 g (0.028 mol) propyl (chlorosulfenyl)(isopropyl)carbamate over a period of 15 minutes. Pyridine hydrochloride forms immediately during addition of the sulfenyl chloride. The reaction mixture was stirred for an additional half hour at room temperature after the addition of the sulfenyl chloride.

The mixture was diluted with 100 ml ether, washed four times with water (25 ml each), and finally the ether solution was dried over anhydrous sodium sulfate. The ether was removed under water pump pressure, and the residue was crystallized from benzene-hexane solvent mixture. Recrystallization from benzene resulted in 5.5 g (62% yield) of product m.p. 68°-70°.

Nmr spectrum in chloroform-d-TMS showed the following absorptions: δ centered at 6.35 (d, 1H, PNH) (J=22 Hz); this absorption clearly indicates that monosubstitution occurs on the nitrogen atom of the phosphoramidate, δ 4.6–4.1 (m, 1H, isopropyl CH), δ 4.2–3.95 (t, 2H, C(O)OCH$_2$) (J=7 Hz), δ 3.8–3.6 (d, 3H, POCH$_3$) (J=12 hz), δ 2.4–2.1 (d, 3H, PSCH$_3$) (J=15 Hz), δ 1.9–1.55 (m, 2H, CH$_2$), δ 1.3–1.2 (d, 6H, isopropyl CH$_3$) (J=7 Hz), δ 1.1–0.85 (t, 3H, CH$_3$) (J=7 Hz).

EXAMPLE II

Synthesis of O,S-dimethyl N-(N'-methoxycarbonyl-N'-ethylaminosulfenyl)phosphoramidothioate To a solution of O,S-dimethyl phosphoramidothioate (4.0 g, 0.028 mol) in 15 ml dichloromethane, was added pyridine (2.2 g, 0.028 mol). The solution was stirred and cooled to 0° C. by the aid of an ice-salt bath. Methyl (chlorosulfenyl)(ethyl)carbamate (4.5 g, 0.027 mol) was added dropwise while stirring. After the complete addition of the sulfenyl chloride, the temperature was allowed to rise up to room temperature, and stirring was continued for an additional hour. Workup of the reaction mixture and purification of the final product were carried out similarly to example I.

Nmr of the final product in chloroform-d-TMS showed the following absorptions: δ 1.4–1.1 (t, 3H, CH$_3$) (J=8 Hz), 2.5–2.2 (d, 3H, PSCH$_3$) (J=16 Hz) 3.95–3.75 (d, 3H, POCH$_3$) (J=12 Hz), 3.85 (s, 3H, OCH$_3$) 6.9–6.5 (d, 1H, PNH) (J=22 Hz), δ 3.6–4.2 (m, 2H, SNCH$_2$).

EXAMPLE III

Synthesis of O,S-dimethyl N-(N'-methoxycarbonyl-N'-n-butylaminosulfenyl)-phosphoramidothioate.

To a solution of O,S-dimethyl phosphoramidothioate (3.5 g, 0.025 mol) in 15 ml of dichloromethane, was added pyridine (2.2 g, 0.028 mol) and the mixture was cooled to 0° C. Methyl (chlorosulfenyl)(n-propyl)carbamate (4.6 g, 0.025 mol) was added dropwise with stirring. After the complete addition of the carbamate, the mixture was stirred at room temperature for an additional hour. Workup of the reaction mixture and purification of the final product were carried out similarly to example I.

Nmr of the final product in chloroform-d-TMS showed the following absorptions: δ 0.75–1.0 (t, 3H, CH$_3$) (J=7 Hz), 1.3–1.9 (m, 2H, CH$_2$), 2.1–2.35 (d, 3H, PSCH$_3$) (J=15 Hz), 3.5–3.9 (m, 2H, SNCH$_2$), 3.65–3.85 (d, 3H, POCH$_3$) (J=13 Hz), 3.75 (S, 3H, OCH$_3$), 6.35–6.7 (d, 1H, PNH) (J=22 Hz).

Other compounds of the invention according to formula (1) above were prepared employing procedure similar to that described in the examples above. Those compounds which are liquid at room temperature were partially purified by several washings with hexane. The product obtained after these washings showed more than 90% purity as evident from their nmr spectra. However, samples of analytical purity were obtained using preparative thin layer chromatography with ether-hexane (3:1) as the developing solvent.

Particularly preferred compounds of the invention are the following:

O,S-Dimethyl N-[N'-(ethoxycarbonyl)-N'-(isopropylaminosulfenyl)]phosphoramidothioate O,S-Dimethyl N-[N'-(isopropoxycarbonyl)-N'-(isopropylaminosulfenyl)]phosphoramidothioate O,S-Dimethyl N-[N'-(n-propoxycarbonyl)-N'-isopropylaminosulfenyl)]phosphoramidothioate O,S-Dimethyl N-[N'-(ethoxycarbonyl)-N'-(tert.-butylaminosulfenyl)]phosphoramidothioate O,S-Dimethyl N-[N'-(n-propoxycarbonyl)-N'-tert.-butylaminosulfenyl)]phosphoramidothioate Table I below sets forth examples of compounds of the invention according to formula (1) above, identified by their respective R$_1$ and R$_2$ structures, and including the melting points and elemental analyses of such compounds.

TABLE I

Physical properties and elemental analysis of O,S-dimethyl N-(N'-alkoxycarbonyl-N'-alkylaminosulfenyl)phosphoramidothioates.

| Compound | R$_1$ | R$_2$ | m.p. | Analysis Calcd. | Found |
|---|---|---|---|---|---|
| 1 | CH$_3$ | C$_2$H$_5$ | liquid | C, 26.27 H, 5.51 | |
| 2 | C$_6$H$_{13}$ | C$_2$H$_5$ | liquid | C, 38.36 H, 7.32 | 38.64 7.5 |
| 3 | CH$_3$ | C$_3$H$_7$ | liquid | C, 29.16 H, 5.94 | |
| 4 | C$_2$H$_5$ | C$_3$H$_7$ | liquid | C, 31.80 H, 6.33 | |
| 5 | C$_3$H$_7$ | C$_3$H$_7$ | liquid | C, 34.16 H, 6.69 | 34.87 7.39 |
| 6 | C$_2$H$_5$ | CH(CH$_3$)$_2$ | 65–7 | C, 31.80 H, 6.33 | 32.11 6.25 |
| 7 | CH(CH$_3$)$_2$ | CH(CH$_3$)$_2$ | 76–8 | C, 34.16 H, 6.69 | 34.96 7.10 |
| 8 | C$_3$H$_7$ | CH(CH$_3$)$_2$ | 68–70 | C, 34.16 H, 6.69 | 34.79 6.38 |
| 9 | C$_2$H$_5$ | C(CH$_3$)$_3$ | 104–6 | C, 34.16 H, 6.69 | 34.33 6.39 |
| 10 | C$_3$H$_7$ | C(CH$_3$)$_3$ | 81–2 | C, 36.35 H, 7.02 | 36.61 7.13 |

The N-[(alkoxycarbonyl)(alkyl)aminosulfenyl]phosphoramidothioates of the invention are stable and can be stored at room temperature for several months without apparent decomposition. Further, while the parent material, methamidophos, is freely soluble in water, the compounds of the invention are substantially less water soluble and when applied as an insecticide to plants or agricultural crops, are not readily removed therefrom by rain and moisture. However, they still maintain the systemic activity of methamidophos.

The insecticidal sulfenyl derivatives of phosphoramidothioate esters of the invention may be formulated with the usual carriers, including additives and extenders used in the preparation of insecticidal compositions. Thus, the toxicants of this invention, like most insecticidal agents, are generally not applied full strength, but are incorporated with the adjuvants and carriers normally employed for facilitating the dispersion of active ingredients, recognizing the accepted fact that the formulation and mode of application of a toxicant may affect the activity of the material.

The present compounds may be made into liquid concentrates by solution or emulsification in suitable liquids such as organic solvents, and into solid concentrates by admixing with talc, clays and other known solid carriers used in the insecticide art. These concentrates are compositions containing about 5–50% toxicant and the rest inert material which includes dispersing agents, emulsifying agents, and wetting agents. The concentrates are diluted for practical application, with water or other liquid for liquid sprays or with additional solid carrier for application as a dust or granular formulation.

The concentration of the toxicant in the dilution generally used for application is normally in the range of about 2% to about 0.001%. Many variations of spraying and dusting compositions in the art may be used, by substituting a compound of this invention into the compositions known or apparent to the art.

Insecticidal compositions may be formulated and applied with other active ingredients, including other insecticides, nematicides, acaricides, fungicides, plant regulators, fertilizers, etc. In applying the chemicals, it is obvious that an effective amount and concentration of the carbamate ester compounds of the invention should be employed.

BIOLOGICAL ACTIVITY

Representative compounds of the invention were tested for insecticidal activity against house flies, *Musca domestica*. Stock 1% concentrated solutions of each of the test compounds were made in acetone, and such solutions diluted with acetone to a concentration of 0.001–0.1%. House flies were treated topically on the notum by 1 μl of each of the diluted acetone solutions and percent mortality was counted 24 hours after application. The insects were held at a constant temperature of 60° F. Results are given as $LD_{50}$ in μg/g.

Mammalian toxicity was determined against Swiss white mice. The test compound was applied orally using corn oil as the carrier. Results are given as $LD_{50}$ in mg of compound per kg body weight. The toxicological data for a number of carbamates of the invention are summarized in Table II.

The term "$LD_{50}$" respresents the dose needed to kill 50% of the test animals. In interpreting the values in Table II below, the lower the value of $LD_{50}$ for house flies, the greater the insecticidal potency or toxicity of that particular compound. On the other hand, the higher the value of $LD_{50}$ for mice, the lower the mammalian toxicity or the greater is the mammalian safety of such compound.

TABLE II

Toxicity of O,S-dimethyl N-(N'-alkoxycarbonyl-N'-alkylaminosulfenyl)phosphoramidothioates to house flies and mice.

| Compound | House fly $LD_{50}$ μ g/g | Mouse (oral) $LD_{50}$ mg/kg |
|---|---|---|
| Methamidophos | 1.3 | 14 |
| 1 | 2.8 | 30 |
| 2 | 3.8 | 34 |
| 3 | 1.6 | |
| 4 | 2.0 | |
| 5 | 1.9 | 36 |
| 6 | 1.9 | 50 |
| 7 | 2.7 | |
| 8 | 2.5 | 50 |
| 9 | 2.5 | 50 |
| 10 | 1.6 | 50 |

From Table II above, it is seen that the sulfenyl derivatives of methamidophos, according to the invention, have insecticidal toxicity comparable with that of the parent material, methamidophos. However, and of significance, the mammalian toxicity of the invention compounds, particularly compounds 6, 8, 9 and 10 of Table II above, is lower, as indicated by their $LD_{50}$ value of 50 for mice, as compared to the higher toxicity as indicated by an $LD_{50}$ value of 14, found for the parent insecticide, methamidophos. Thus, Table II shows that the sulfenyl derivatives of phosphoramidothioate esters of the invention have high insecticidal activity or potency, but have reduced mammalian toxicity or greater mammalian safety.

While we have described particular embodiments of the invention for purposes of illustration, it will be understood that various changes and modifications within the spirit of the invention can be made, and the invention is not to be taken as limited except by the scope of the appended claims.

What is claimed is:

1. N-[(alkoxycarbonyl)(alkyl)aminosulfenyl]phosphoramidothioates of the formula $$\begin{array}{c} CH_3O \\ \phantom{xx} \diagdown \phantom{x} \diagup\!\!\!O \\ \phantom{xxxxx} P \\ \phantom{xx} \diagup \phantom{x} \diagdown \phantom{xxxxxxx} O \\ CH_3S \phantom{xxxx} N-S-N-\overset{\|}{C}-OR_1 \\ \phantom{xxxxxxxxxx} | \phantom{xxx} | \\ \phantom{xxxxxxxxxx} H \phantom{xxx} R_2 \end{array}$$

where $R_1$ is alkyl containing from 1 to 12 carbon atoms and $R_2$ is alkyl containing 2 to 8 carbon atoms.

2. Compounds as defined in claim 1, wherein $R_1$ contains from 1 to 8 carbon atoms, and $R_2$ contains from 2 to 4 carbon atoms.

3. Compounds as defined in claim 1, wherein $R_1$ and $R_2$ can be straight chain or branched chain alkyl groups.

4. Compounds as defined in claim 2, wherein $R_1$ and $R_2$ can be straight chain or branched chain alkyl groups.

5. Compounds as defined in claim 2, wherein $R_1$ is an alkyl group free from nonaromatic unsaturation.

6. Compounds as defined in claim 1, wherein $R_2$ is a branched chain alkyl.

7. Compounds as defined in claim 2, wherein $R_2$ is selected from the group consisting of isopropyl and tert.-butyl.

8. Compound as defined in claim 1, which is O,S-dimethyl N-[N'-(ethoxycarbonyl)-N'-(isopropylaminosulfenyl)]phosphoramidothioate.

9. Compound as defined in claim 1, which is O,S-dimethyl N-[N'-(isopropoxycarbonyl)-N'-(isopropylaminosulfenyl)]phosphoramidothioate.

10. Compound as defined in claim 1, which is O,S-dimethyl N-[N'-(n-propoxycarbonyl)-N'-isopropylaminosulfenyl)]phosphoramidothioate.

11. Compound as defined in claim 1, which is O,S-dimethyl N-[N'-(ethoxycarbonyl)-N'-(tert.-butylaminosulfenyl)]phosphoramidothioate.

12. Compound as defined in claim 1, which is O,S-dimethyl N-[N'-(n-propoxycarbonyl)-N'-tert.-butylaminosulfenyl)]phosphoramidothioate.

13. The method of controlling insects which comprises applying to the sites of infestation an insecticidally effective amount of a compound as defined in claim 1.

14. The method of controlling insects which comprises applying to the sites of infestation an insecticidally effective amount of a compound as defined in claim 2.

15. An insecticidal composition comprising an insecticidally effective amount of a compound as defined in claim 1, in admixture with a carrier.

16. An insecticidal composition comprising an insecticidally effective amount of a compound as defined in claim 2, in admixture with a carrier.

17. A method for the preparation of N-[(alkoxycarbonyl)(alkyl)aminosulfenyl]phosphoramidothioates of the formula

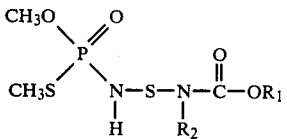

which comprises reacting the compound of the formula

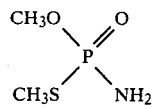

with a compound having the formula

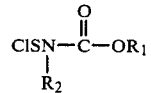

where $R_1$ is alkyl containing from 1 to 12 carbon atoms and $R_2$ is alkyl containing 2 to 8 carbon atoms.

18. The method as defined in claim 17, the reaction taking place in the presence of an HCl acceptor and at temperature ranging from 0° C. to about 20° C.

19. The method as defined in claim 18, said HCl acceptor being pyridine and said reaction taking place in an organic solvent.

* * * * *